United States Patent [19]

Kienzle

[11] 4,156,090

[45] May 22, 1979

[54] POLYENE COMPOUNDS

[75] Inventor: Frank Kienzle, Therwil, Switzerland

[73] Assignee: Hoffmann-La Roche Inc., Nutley, N.J.

[21] Appl. No.: 741,324

[22] Filed: Nov. 12, 1976

[30] Foreign Application Priority Data

Nov. 30, 1975 [CH] Switzerland ............... 15465/75

[51] Int. Cl.² ............................................. C07C 69/00
[52] U.S. Cl. .................................... 560/61; 560/129; 560/131; 560/226; 568/823; 568/828; 260/448.8 R; 260/448.2 B
[58] Field of Search ............ 560/61, 129, 231, 226; 260/617 R; 568/823, 828

[56] References Cited

U.S. PATENT DOCUMENTS

| | | | |
|---|---|---|---|
| 3,299,111 | 1/1967 | Adams et al. | 560/129 X |
| 3,917,675 | 11/1975 | Ochsner | 560/231 |
| 4,000,198 | 12/1976 | Rosenberger | 260/586 R |

*Primary Examiner*—Paul F. Shaver
*Attorney, Agent, or Firm*—Jon S. Saxe; Bernard S. Leon; William H. Epstein

[57] ABSTRACT

15,15'-Didehydro-astaxanthin and ester derivatives thereof useful as coloring agents and intermediates for astaxanthin and a method for preparing astaxanthin from keto α-isophorone and intermediates therein.

13 Claims, No Drawings

POLYENE COMPOUNDS

SUMMARY OF INVENTION

In accordance with this invention, there has been discovered a synthesis for a compound of formula

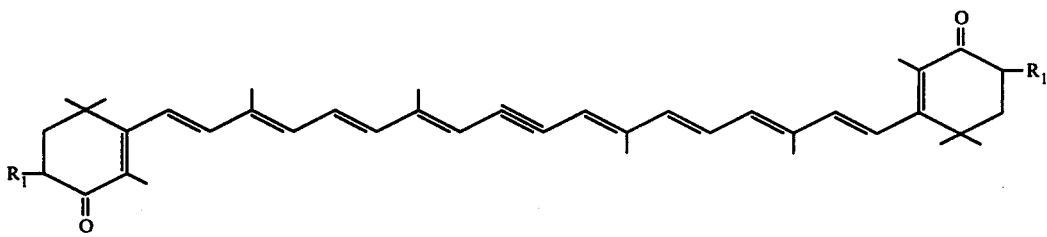

wherein $R_1$ is hydroxy or acyloxy and partially hydrogenated products thereof from α-isophorone.

The compound of formula I embraces both racemic and optically active polyene compounds.

The compounds of formula I are orange-red coloring agents which are suitable for coloring foodstuffs and pharmaceutical and cosmetic preparations. They are also starting compounds for the manufacture of racemic and naturally occurring, optically active astaxanthin. Astaxanthin is a red dyestuff which is widespread in nature, particularly in Crustacea, but is present in low concentrations and can only be isolated with difficulty and in an unsatisfactory yield. Partial synthesis, e.g. the oxidation of crustaxanthin, yield only small quantities of astaxanthin and total synthesis cannot proceed past the initial stages.

The present process, which comprises using novel starting compounds, overcomes all synthesis deficiencies encountered hitherto.

Astaxanthin can be obtained from the compounds of formula I by partial hydrogenation and, if necessary, saponification, and can be present in the racemic or optically active form, depending on the starting material.

Racemic astaxanthin can be characterized by the formula

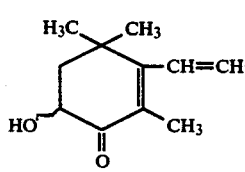—CH=CH—$\overset{CH_3}{\underset{|}{C}}$=CH—CH=CH—$\overset{CH_3}{\underset{|}{C}}$=CH—CH=CH—CH=C—CH=CH—CH=C—CH=CH—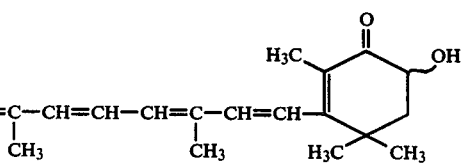

naturally occurring, optically active astaxanthin, i.e. 3(S), 3'(S)-astaxanthin, can be characterized by the formula

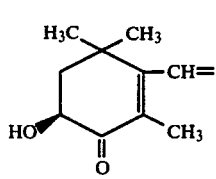—CH=CH—$\overset{CH_3}{\underset{|}{C}}$=CH—CH=CH—$\overset{CH_3}{\underset{|}{C}}$=CH—CH=CH—CH=C—CH=CH—CH=C—CH=CH—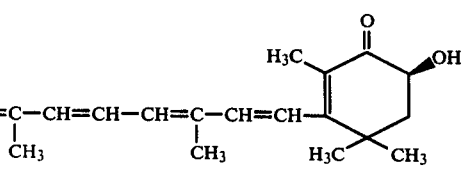

DETAILED DESCRIPTION

The symbol ▶ indicates that the bond represented by this symbol is in front of the plane of the molecule. The symbol ∼ indicates that the bond represented by this symbol can be both in front of and behind the plane of the molecule.

According to the present invention, the polyene compounds of formula I can be manufactured by condensing a compound of the general formula

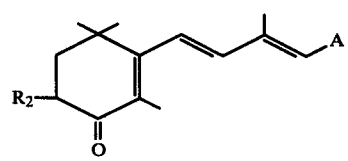

with a compound of the general formula

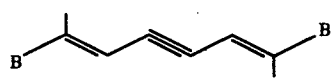

wherein $R_2$ is an acyloxy; one of A and B is formyl and the other is triarylphosphonium methyl having the formula $-CH_2-P[X]_3^{\oplus}Y^{\ominus}$; X is aryl; and Y is the anion of an inorganic or organic acid,
to give a polyene compound of formula I and, if desired, hydrolyzing any acyloxy group which is present in the condensation product of formula I and which can be saponified to the hydroxy group.

The triple bond present in the condensation product of formula I can, if desired, be hydrogenated to the double bond.

The condensation components of formulae II and III, namely (a) aldehyde of the general formula

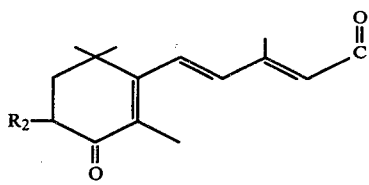
(IIA)

wherein R₂ is as above; given and phosphonium salts of the general formula

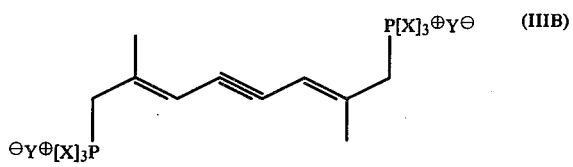
(IIIB)

wherein X and Y are as above; or (b) phosphonium salts of the general formula

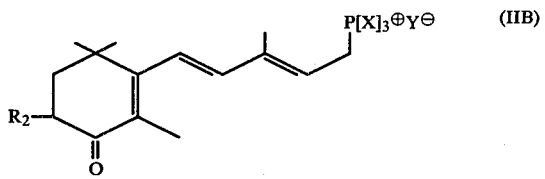
(IIB)

wherein R₂, X and Y are as above, and the aldehyde of the formula

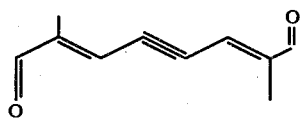

are condensed with one another under the conditions of a Wittig condensation in the presence of an acid binding agent (e.g. in the presence of an alkali metal alcoholate such as sodium methylate, lithium carbonate or sodium bicarbonate) or in the presence of an optionally alkyl-substituted alkylene oxide, in particular in the presence of ethylene oxide or 1,2-butylene oxide, appropriately in a solvent (e.g. in an alkanol such as isopropanol, in a halogenated hydrocarbon such as methylene chloride or in dimethylformamide) and at a temperature between room temperature and the boiling point of the condensation mixture.

The acyloxy groups R₁ and R₂ are derived from lower and higher alkanecarboxylic and alkenecarboxylic acids which can be unsubstituted or substituted with halogen atoms or alkoxy or aryloxy groups. Among the acyl groups are included lower alkanoyloxy which contains from 1 to 6 carbon atoms or lower alkenoyloxy groups which contain from 2 to 6 caron atoms and higher alkenoyloxy or alkanoyloxy which contains from 7 to 20 carbon atoms. Both the lower and higher alkanoyloxy or alkenoyloxy groups can be unsubstituted or substituted with halogen, alkoxy or aryloxy substituents. Among the preferred substituted and unsubstituted lower alkanoyloxy or alkenoyloxy groups are included acetoxy, propionyloxy, butyryloxy, valeryloxy, capryloxy, monochloroacetoxy, di- chloroacetoxy, ethoxyacetoxy and phenoxyacetoxy. Among the preferred higher substituted and unsubstituted acyloxy groups are included palmitoyloxy, stearoyloxy, oleoyloxy, α-chloropalmitoyloxy, α-ethoxypalmitoyloxy and α-phenoxypalmitoyloxy groups.

Only the acyloxy groups substituted by halogen atoms or alkoxy or aryloxy groups can be saponified in the present system to the hydroxy group without this being partially converted into the oxo group during the saponification.

The acyloxy groups mentioned hereinbefore accordingly embrace both acyloxy groups which can be converted into hydroxy groups and acyloxy groups which cannot be converted into hydroxy groups.

The acyloxy groups substituted by chlorine or phenoxy which are specifically mentioned hereinbefore are preferred groups. The trichloroacetoxy and trifluoroacetoxy groups have proved to be less suitable because they are too labile.

The acyl groups which can be removed hydrolytically from the acyloxy groups of the condensation product of formula I can be split off in a manner which is known per se. Because of the susceptibility of the molecule, the hydrolysis of the acyloxy groups is carried out as carefully as possible. The acyloxy groups mentioned hereinbefore can be saponified to the hydroxy group without difficulty by treatment with weak alkali at a temperature between about −30° C. and about +50° C. The monochloroacetoxy and dichloroacetoxy groups can be hydrolyzed by simply heating in water or in an aqueous alkanol.

If the Wittig condensation, described in more detail hereinbefore, of the compounds of formulae II and III is carried out in a protic solvent, such as isopropanol, an acyl group which is present and which can easily be removed hydrolytically is split off under the condensation conditions and a compound of formula I in which R₁ is hydroxy is obtained.

If, on the other hand, the Wittig condensation is carried out in an aprotic solvent, such as diethyl ether or methylene chloride, even acyl groups which can easily be removed hydrolytically remain unchanged under the condensation conditions, and a compound of formula I in which R₁ represents acyloxy is obtained.

The condensation components of formulae IIA and IIB are novel compounds. They can be synthesized from the same starting compound of the formula

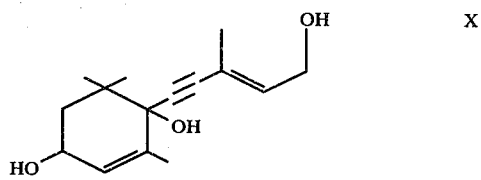
X which is also novel. The starting compound of formula X embraces racemic and optically active compounds.

If the racemic compound of formula X is used as the starting compound, a racemic aldehyde of formula IIA and a racemic phosphonium salt of formula IIB are obtained, and, by condensing these racemates with the condensation components of formulae IIIB and IIIA respectively, a recemic condensation product of formula I is subsequently obtained, which can be converted into racemic astaxanthin by partial hydrogenation and, if necessary, saponification.

Alternatively, if the optically active 4(S)-compound of the formula

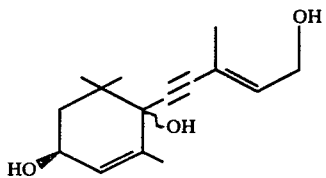
(XA)

is used as the starting compound, a 4(S)-aldehyde of formula IIA and a 4(S)-phosphonium salt of formula IIB are obtained, and, by condensing these optically active compounds with the condensation components of formulae IIIB and IIIA respectively, an optically active condensation product of formula I is subsequently obtained, which can be converted into the naturally occurring optically active 3(S), 3'(S)-astaxanthin by partial hydrogenation and, if necessary, saponification.

The synthesis of the starting compounds IIA and IIB starting from the compound of formula X, which also embraces the compound of formula XA, is illustrated by the following reaction scheme, in which $R_2$ has the significance given earlier:

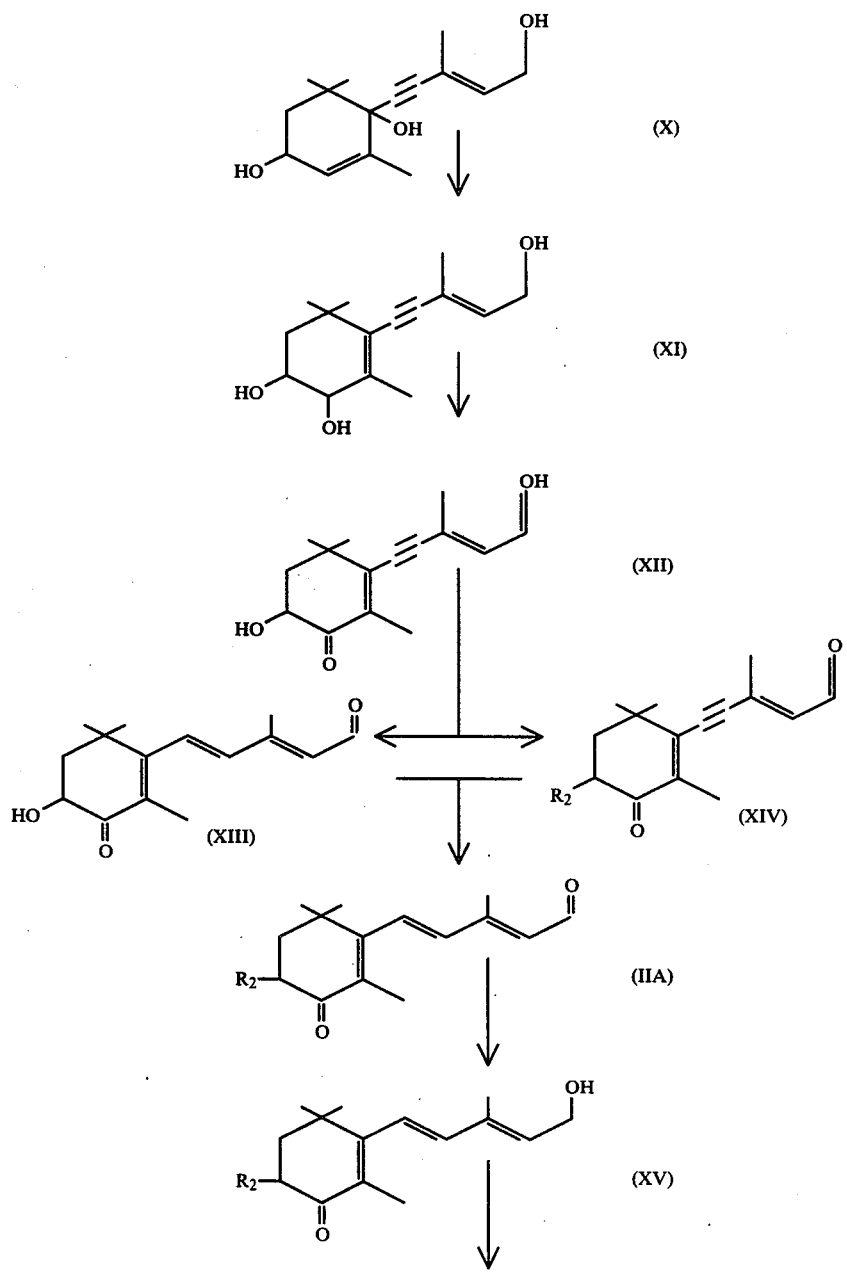

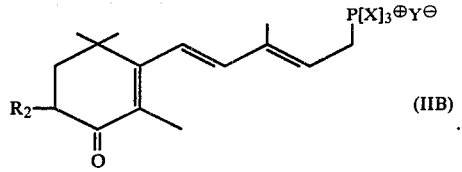

(IIB)

The preparation of the starting compounds of formulae IIA and IIB is described in detail in the following text:

The compound of formula X, namely 5-[2,6,6-trimethyl-1,4-dihydroxycyclohex-2-en-1-yl]-3-methyl-penta-2-en-4-yn-1-ol, is converted by an allyl rearrangement into 5-[2,6,6-trimethyl-3,4-dihydroxy-cyclohex-1-en-1yl]-3-methyl-penta-2-en-4-yn-1-ol (XI). The allyl rearrangement is appropriately carried out in an aqueous mineral acid (e.g. sulfuric acid or a hydrohalic acid such as hydrochloric acid) optionally in the presence of a solvent (e.g. acetone or tetrahydrofuran), or in an organic acid (e.g. formic acid or acetic acid). If the rearrangement is carried out in an organic acid, the ester formed intermediately must be saponified (e.g. with an aqueous sodium carbonate solution).

The resulting triol of formula XI is oxidized to 5-[2,6,6-trimethyl-3-oxo-4-hydroxy-cyclohex-1-en-1yl]-3-methyl-penta-2-en-4-yn-1-al (XII). The oxidation can be carried out, for example, using nikel peroxide or manganese dioxide. A 2,3-dichloro-5,6-dicyano-benzoquinone is a particularly preferred oxidizing agent. The oxidation is appropriately carried out in an inert organic solvent. Any conventional inert organic solvent can be utilized. Among the preferred solvents are diethyl ether, ethyl acetate, dioxane and benzene. The temperature of the reaction is not critical and any temperature between −30° C. and the boiling point of the mixture can be utilized in carrying out this reaction.

The resulting hydroxyaldehyde of formula XII is either partially hydrogenated and then esterified, or esterified and then partially hydrogenated. The sequence in which the partial hydrogenation of the acetylene compound and the protecting of the hydroxy group is carried out is determined by the choice of the esterifying agent. If a halogenated alkanyl or alkenyl carboxylic acid is used as the esterifying agent (e.g. monochloroacetic or dichloroacetic acid), the halogen atoms of which can poison the catalyst, it is advisable to partially hydrogenate the hydroxyaldehyde of formula XII and then to esterify the product. If on the other hand an unhalogenated esterifying agent is used, the hydroxyaldehyde of formula XII can be esterified and the product then partially hydrogenated.

The partial hydrogenation of the ethynylene group to the vinylene group is carried out it a manner which is known per se using partially poisoned palladium catalyst [Lindlar catalyst] in a solvent (e.g. benzene, toluene or ethyl acetate) or in an alkanol (e.g. methanol or isopropanol) and appropriately under normal pressure and at room temperature.

The protecting of the hydroxy group by esterification with a lower or higher alkanecarboxylic or alkenecarboxylic acid anhydride or halide which can be unsubstituted or substituted by halogen, alkoxy or aryloxy groups is appropriately carried out in an inert organic solvent (e.g. tetrahydrofuran or ethyl acetate) in the presence of an organic nitrogen base (e.g. pyridine or triethylamine) at a temperature between about −30° C. and +50° C.

The acyloxyaldehyde obtained from the hydroxyaldehyde of formula XII by partial hydrogenation and esterification, or esterification and partial hydrogenation, via compounds of formulae XIII and XIV respectively is the starting compound IIA of process variant (a) of the present process.

The starting compound of formula IIB of process variant (b) can be prepared from the acyloxyaldehyde of formula IIA as follows:

The aldehyde of formula IIA is reduced to the alcohol of formula XV by treatment with a reducing agent (e.g. sodium borohydride in ethanol, dimethylformamide, tetrahydrofuran or diethylene glycol dimethyl ether or sodium dihydro bis[2-methoxyethoxy]-aluminate or diisobutylaluminium hydride in tetrahydrofuran or dimethyl ether). The reduction of the oxo group to the hydroxy group is carried out at a temperature below 0° C., preferably at −30° C.

The resulting alcohol of formula XV is converted into the corresponding halide by treatment with a halogenating agent (e.g. phosphorus tribromide, phosphorus oxychloride, thionyl chloride or phosgene in a diethyl ether or dimethylformamide) and the halide is then converted into the phosphonium salt of formula IIB employed in process variant (b) by reaction with a triarylphosphine (e.g. triphenylphosphine).

The starting compound for the preparation of compounds of formulae IIA and IIB, namely the triol of formula X, can be prepared by various methods, depending on whether the racemate or the optically active 4(S)-diastereomer is desired.

The racemate of formula X can be prepared from keto-α-isophorone, as illustrated in the following reaction scheme:

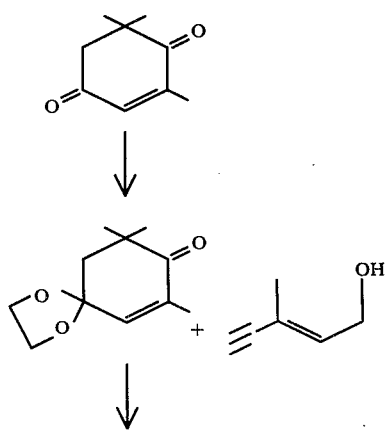

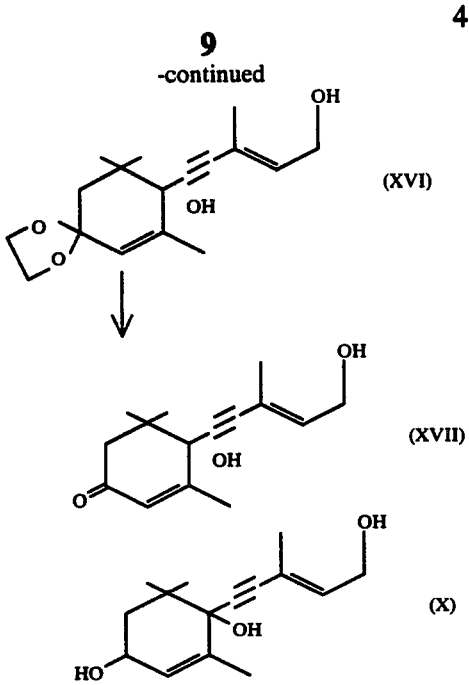

The reaction steps illustrated in the reaction scheme hereinbefore can be carried out as follows:

Keto-α-isophorone is acetalized. The resulting 7,9,9-trimethyl-1,4-dioxaspiro[4,5]dec-6-en-8-one is condensed with trans-1-hydroxy-3-methyl-pent-2-en-4-yne in the presence of lithium in liquid ammonia and iron-(III) nitrate in ether to give rac. 8-(5-hydroxy-3-methyl-pent-3-en-1-yn-1-yl)-7,9,9-trimethyl-1,4-dioxaspiro[4,5]-dec-6-en-8-ol (XVI).

The resulting acetal of formula XVI is hydrolyzed to rac. 5-(1-hydroxy-4-oxo-2,6,6-trimethyl-cyclohex-2-en-1-yl)-3-methyl-penta-2-trans-en-4-yn-1-ol (XVII) by treatment with an acid, preferably with a mineral acid (e.g. sulfuric acid), in a solvent (e.g. in acetone or tetrahydrofuran) at room temperature.

The resulting ketone of formula XVII is reduced to rac. 5-(2,6,6-trimethyl-1,4-dihydroxy-cyclohex-2-en-1-yl)-3-methyl-penta-2-en-4-yn-1-ol (X) by treatment with a reducing agent (e.g. sodium borohydride in ethanol, dimethylformamide, tetrahydrofuran or diethylene glycol dimethyl ether) at room temperature.

The optically active 4(S)-diastereomer of formula X can be prepared from 4(R), 6(R)-4-hydroxy-2,6,6-trimethyl-cyclohexanone, as illustrated in the following reaction scheme in which $R_3$ is alkanoyl or aroyl; and $R_4$ is lower alkyl:

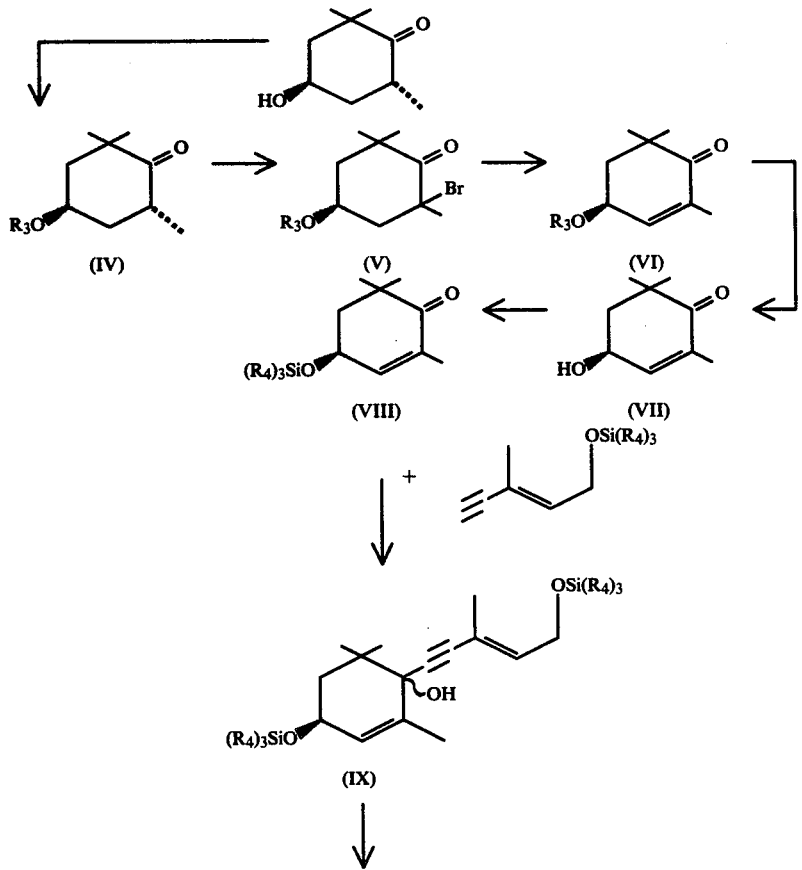

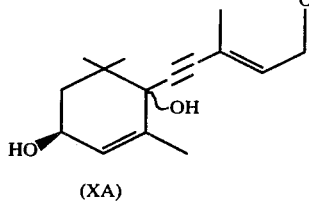

(XA)

The reaction steps illustrated in the reaction scheme hereinbefore can be carried out as follows:

4(R), 6(R)-4-Hydroxy-2,6,6-trimethyl-cyclohexanone is reacted with acetic anhydride in an organic nitrogen base, preferably pyridine, at room temperature to give 4(R), 6(R)-4-acetoxy-2,6,6-trimethyl-cyclohexanone (IV).

The resulting compound of formula IV is brominated by treatment with bromine in glacial acetic acid, while cooling, to give 4(S)-2-bromo-2,6,6-trimethyl-4-acetoxy-cyclohexanone (V).

The resulting compound of formula V is debrominated by treatment with lithium carbonate and lithium bromide in dimethylformamide at an elevated temperature, preferably at 80° C., hydrogen bromide being split off and a carbon-carbon double bond being formed to give 4(S)-2,6,6-trimethyl-4-acetoxy-cyclohex-2-en-1-one (VI).

The resulting compound of formula VI is hydrolyzed in an aqueous alkanol (e.g. in methanol), using an alkali metal hydroxide or alkali metal carbonate, at room temperature to give 4(S)-2,6,6-trimethyl-4-hydroxy-cyclohex-2-en-1-one (VII).

The hydroxy group of the resulting compound of formula VII is protected by treatment with trimethylchlorosilane in the presence of an organic nitrogen base (e.g. triethylamine) in diethyl ether at about 0° C. to give 4(S)-2,6,6-trimethyl-4-[(trimethylsilyl)oxy]-cyclohex-2-en-1-one (VIII).

The resulting compound of formula VIII is condensed with trimethyl-[(trans-3-methyl-penta-2-en-4-yn-1-yl)oxy]-silane in a solvent (e.g. in tetrahydrofuran) via a Grignard reaction to give 4(S)-5-[2,6,6-trimethyl-1-hydroxy-4-[(trimethyl-silyl)-oxy]-cyclohex-2-en-1-yl]-3-methyl-1-[(trimethyl-silyl)oxy]-penta-2-en-4-yne (IX).

The silyl ether of formula IX is saponified in an alkanol (e.g. methanol) by shaking with a dilute aqueous alkali metal hydroxide solution at room temperature to give optically active 4(S)-5-(2,6,6-trimethyl-1,4-dihydroxy-cyclohex-2-en-1-yl)-trans-3-methyl-penta-2-en-4-yn-1-ol (XA).

The trimethyl-[(trans-3-methyl-penta-2-en-4-yn-1-yl)oxy]-silane used hereinbefore in the condensation reaction with the compound of formula VIII can be prepared in a simple manner by treatment of trans-3-methyl-penta-2-en-4-yne with trimethyl-chlorosilane in an ether solvent (e.g. dimethyl ether) in the presence of an organic nitrogen base (e.g. triethylamine) at room temperature.

However, if the silyloxyketone of formula VIII is condensed with trimethyl-[(cis-3-methyl-penta-2-en-4-yn-1-yl)-oxy]-silane prepared from cis-3-methyl-penta-2-en-4-yne and trimethylchlorosilane - the corresponding cis-compound of formula XA is obtained, via the cis-silyl ether of formula IX, and from this the cis-compounds of formulae IIA and IIB. These cis-compounds of formulae IIA and IIB can be isomerized in a simple manner, for example by treatment with palladium oxide, before or after the condensation with the compounds of formulae IIIC and IIIB respectively.

The term "halogen" as used throughout the specification designates all four halogens, i.e., chlorine, fluorine, bromine and iodine. The term "lower alkyl" designates alkyl groups containing from 1 to 6 carbon atoms such as methyl, ethyl, propyl, isopropyl, etc. The term "lower alkoxy" designates alkoxy substituents containing from 1 to 6 carbon atoms such as methoxy, ethoxy, propoxy, isopropoxy, etc.

The term aryl signifies both mononuclear aromatic hydrocarbon groups such as phenyl, tolyl, etc. or polynuclear aryl groups such as naphthyl, anthryl, azulyl, etc. The term aralkyl includes aralkyl groups where aryl is defined as above. The preferred aralkyl group is benzyl. The term alkanoyl includes lower alkanoyl containing from 2 to 6 carbon atoms formed by removal of the hydroxy moiety from the lower alkane carboxylic acids mentioned hereinbefore and higher alkanoyl containing from 7 to 20 carbon atoms formed by removal of the hydroxy moiety from the higher alkane carboxylic acids mentioned hereinbefore. The term aroyl includes aroyl groups where aryl is defined hereinbefore. Among the preferred aroyl groups is benzoyl.

The coloring agents of Formula I above, in accordance with this invention, can be used to color any conventional foodstuff including beverages, fruits, vegetable preserves, marmalades, cream foods, confectionary, edible fats, cheese, fish products, pasta, soup powders etc. Any conventional pharmaceutical preparation can be colored by compounds of Formula I. Among the typical pharmaceutical preparations which can be colored in accordance with this invention are included dragees, suppositories, gelatin capsules and syrups. Also any conventional cosmetic preparation can be colored with the compounds of Formula I above. Among the conventional cosmetic preparations which can be colored in accordance with this invention are included, toothpaste, skin creams, lipsticks and non-alcoholic mouthwashes.

In coloring materials such as foodstuffs, cosmetic and pharmaceutical preparations, the compounds of Formula I above should be added to the material. Generally, it is preferred that the foodstuff, pharmaceutical and cosmetic preparation contains from about 0.0000001 part by weight to about 0.1 part by weight of compound of Formula I above based on the weight of the foodstuff, pharmaceutical and cosmetic preparation.

The polyene compounds of Formula I can be employed for coloring foodstuffs, pharmaceutical and cosmetic preparations both in the original crystalline form and in a particular water-soluble form.

The polyene compounds of Formula I above can chiefly be used in the crystalline form for coloring fats and oils, as well as fat-containing substances such as, for example, marzipan, suppositories, lipsticks. The polyene compounds of Formula I above, can, for example, be dissolved in oils without further ado. Prior to the addition of the pigment, hard or soft fats are conveniently liquidified by heating. Brushable fats may also be colored by kneading-in an oil pigment-solution. Marzipan, which for example, is thoroughly kneaded with a solution of the polyene compound of Formula I in almond oil, can also be colored in the same way. Colored suppositories and lipsticks can, for example, be manufactured in such a way that the polyene compound used as the pigment is stirred into the liquified carrier mass prior to filling into the molds.

For coloring fat-poor or fatless substances, there is generally used a water-dispersible form of the polyene compounds of Formula I. The preparation of these compounds in water-dispersible form can be carried out by any of the techniques disclosed in U.S. Pat. No. 2,861,891, Bauernfeind et al. and U.S. Pat. No. 3,110,598, Muller et al. These include dissolving the polyene compounds of Formula I in a suitable solvent, homogenizing the solution (together with a stabilizer and a solubilizing or emulsifying agent if required, as well as with an animal or vegetable fat if desired) with water in the presence of a protecting colloid and evaporating the emulsion formed to dryness under reduced pressure.

Any conventional organic solvent capable of dissolving the compound of Formula I above, can be utilized. These solvents include volatile halogenated hydrocarbons, such as, for example, chloroform, carbon tetrachloride, methylene chloride, etc. Any conventional antioxidatively active stabilizers can be utilized. These antioxidants include tocopherols, 2,6-ditertbutyl-4-hydroxytoluene [BHT], butyl-hydroxyanisole [BHA].

The salts of fatty acid esters of ascorbic acid (e.g the sodium salt of ascorbyl palmitate), inter alia, have been found to be active as solubilizing agents. Any of the conventional solubilizing agents can be utilized in accordance with this invention. Concerning emulsifying agents, any conventional emulsifying agents can be utilized in accordance with this invention. The polyoxyethylene derivatives of sorbitan anhydrides partially esterified with fatty acids [Tweens] or non-iogenic derivatives of fatty compounds with polyoxyethylene derivatives [Cremophores] are, for example, usable. The protecting colloids in which the compounds of Formula I are emulsified or dispersed include any of the conventional water soluble gelable colloids. Gelatin, dextrin, pectin, tragacanth, guar (especially in the presence of saccharose, glycerin, sorbitol), have, for example, been found to be useful as protecting colloids. The color brilliance of the aqueous solutions can be increased by the addition of any animal fat (e.g. beef tallow) or vegetable oil (e.g. groundnut oil).

The following examples are illustrative but not limitative of the invention. All temperatures are in degrees Centigrade and the ether utilized is diethyl ether.

The term Lindlar catalyst refers to a palladium-calcium carbonate-lead(II)oxide mixture obtained according to a published procedure [H. Lindlar, Helv., 35, 446 (1952)].

EXAMPLE 1

4.4 g of rac. 5-[2,6,6-trimethyl-3-oxo-4-(phenoxyacetoxy)-cyclohex-1-en-1-yl]-3-methyl-penta-2,4-diene-1-triphenyl-phosphonium bromide (IIB) and 0.3 g of 2,7-dimethyl-octa-2,6-dien-4-yne-1,8-dial (IIA) are dissolved in 70 ml of isopropanol. 3.5 ml of 2-N sodium methylate are added and the solution is stirred for 1 hour at room temperature, then poured into water and extracted with methylene chloride. The rac. 15,15'-didehydro-astaxanthin which remains after evaporation of the extract melts, after recrystallization from chloroform/methanol or pyridine/water, at 201°–203° C. U.V. maximum: 454 nm.

EXAMPLE 2

148.8 g of trans-1-hydroxy-3-methyl-but-2-en-4-yne are added dropwise to a solution of 25 g of lithium and 1.5 g of iron-(III) nitrate in 3000 ml of liquid ammonia. 234.5 g of 7,9,9-trimethyl-1,4-dioxaspiro[4,5]dec-6-en-8-one, dissolved in 450 ml of diethyl ether, are added dropwise to the mixture. The ammonia, which evaporates off as the temperature increases, is continually replaced by 3000 ml of diethyl ether. The ethereal solution is stirred for 24 hours at room temperature and then poured into water. The ether phase is separated off and evaporated. The rac. 8-(5-hydroxy-3-methyl-pent-3-en-1-yn-1-yl)-7,9,9-trimethyl-1,4-dioxaspiro[4,5]dec-6-en-1-ol (XVI) which remains melts, after recrystallization from isopropyl ether, at 124°–126° C.

EXAMPLE 3

120 g of the acetal of formula XVI obtained in Example 2 are dissolved in 2000 ml of acetone. 200 ml of 10% strength aqueous surfuric acid are added and the solution is stirred for 20 minutes, then poured into water and extracted with diethyl ether. The viscous rac. 5-(1-hydroxy-4-oxo-2,6,6-trimethyl-cyclohex-2-en-1-yl)-3-methyl-penta-2-en-4-yn-1-ol (XVII) which remains after evaporation of the ether extract is further reacted as follows:

22 g of the ketone of formula XVII are dissolved in 200 ml of methanol. 2 g of sodium borohydride are added and the solution is stirred for 3 hours at room temperature. The residue obtained after evaporation of the methanol solution is taken up in water and extracted with diethyl ether. The isomer mixture of rac. 5-[2,6,6-trimethyl-1,4-dihydroxy-cyclohex-2-en-1-yl]-3-methyl-penta-2-en-4-yn-1-ol (X) which remains after evaporation of the ether extract can be resolved by adsorption on silica gel. The 1,4-trans-diol melts at 105°–106° C. and the corresponding 1,4-cis-diol melts at 115°–116° C.

EXAMPLE 4

62 g of the isomer mixture of formula X obtained in Example 3 are dissolved in 900 ml of methylene chloride. 250 ml of 98% strength formic acid are added and the solution is stirred for 2 hours at room temperature and then poured into water. The methylene chloride phase is separated off and evaporated. The residue is taken up in 1300 ml of methanol. 130 g of potassium carbonate and 650 ml of water are added and the solution stirred for 30 minutes, then poured into a saturated aqueous sodium chloride solution and extracted with ethyl acetate. The crystalline cis/trans mixture of rac. 5-(2,6,6-trimethyl-3,4-dihydroxy-cyclohex-1-en-1-yl)-3-methyl-penta-2-en-4-yn-1-ol (XI) which remains after evaporation of the extract is in the form of two isomers which can be resolved by adsorption on silica gel. The 3,4-trans-diol is an oil and the corresponding 3,4-cis-diol melts at 122°–123° C.

EXAMPLE 5

20 g of the isomer mixture of formula XI obtained in Example 4 are dissolved in 1800 ml of methylene chloride. The solution is poured into a suspension of 700 g of manganese dioxide in 2000 ml of methylene chloride. The mixture is stirred for 45 minutes and then filtered. The rac. 5-(2,6,6-trimethyl-3-oxo-4-hydroxy-cyclohex-1-en-1-yl)-3-methyl-penta-2-en-4-yn-1-al (XII) which remains after evaporation of the filtrate melts, after recrystallization from a 1:1 mixture of ethyl acetate/hexane at 79°–81° C.

EXAMPLE 6

14.2 g of the ketoaldehyde of formula XII obtained in Example 6 are dissolved in 500 ml of ethyl acetate and then hydrogenated under normal pressure and at room temperature, using 4 g of a partially poisoned palladium catalyst. The hydrogenation is discontinued when 1.1 mol equivalents of hydrogen have been absorbed. The solution is separated off from the catalyst and evaporated. The rac. 5-(2,6,6-trimethyl-3-oxo-4-hydroxy-cyclohex-1-en-1-yl)-3-methyl-penta-2,4-dien-1-al (XIII) which remains is purified by adsorption on silica gel and further reacted as follows:

10 g of the hydroxyketoaldehyde of formula XIII obtained hereinbefore are dissolved in 200 ml of ether. 20 ml of pyridine are added to the solution at 0° C. and then 9.0 g of phenoxyacetic acid chloride are added dropwise. The mixture is stirred for 1 hour and then poured into ice-water and extracted with diethyl ether. The ether extract is dried over sodium sulfate and evaporated. The oily rac. 5-[2,6,6-trimethyl-3-oxo-4-(phenoxyacetoxy)-cyclohex-1-en-1-yl]-3-methyl-penta-2,4-dien-1-al (IIA) [IR $u=1760$ cm$^{-1}$] which remains can then be condensed with 2,7-dimethyl-octa-2,6-dien-4-yne-1,8-di-triphenylphosphonium bromide according to the process of the invention to give rac. 15,15'-didehydro-astaxanthin.

EXAMPLE 7

As described in the following, the aldehyde of formula IIA can also be obtained starting from the ketoaldehyde of formula XII. The ketoaldehyde is initially esterfied to the triply unsaturated ketoaldehyde of formula XIV and then reduced to the starting aldehyde of formula IIA:

9.3 g of rac. 5-(2,6,6-trimethyl-3-oxo-4-hydroxy-cyclohex-1-en-1-yl)-3-methyl-penta-2-en-4-yn-1-al (XII) are dissolved in 120 ml of diethyl ether. 4 ml of pyridine are added to the solution at 0° C. and then 7.7 g of phenoxyacetic acid chloride are added dropwise. The mixture is stirred for 1 hour and then poured into ice-water and extracted with diethyl ether. The ether extract is dried over sodium sulfate and evaporated. The oily rac. 5-[2,6,6-trimethyl-3-oxo-4-(phenoxyacetoxy)-cyclohex-1-en-1-yl]-3-methyl-penta-2-en-4-yn-1-al (XIV) which remains is further reacted as follows:

16 g of the triply unsaturated aldehyde of formula XIV obtained hereinbefore are dissolved in 200 ml of toluene and then hydrogenated under normal pressure and at room temperature, using 4 g of a partially poisoned palladium catalyst. The hydrogenation is discontinued when 1.1 mol equivalents of hydrogen have been absorbed. The solution is separated off from the catalyst and evaporated. The aldehyde product rac. 5-[2,6,6-trimethyl-3-oxo-4-(phenoxy-acetoxy)-cyclohex-1-en-1-yl]-3-methyl-penta-2,4-dien-1-al (IIA), remains after evaporation.

EXAMPLE 8

6.0 g of the aldehyde product of formula IIA obtained in Example 7 are dissolved in 70 ml of ethanol. 150 mg of sodium borohydride are added at −30° C. and the solution is stirred for 1 hour and then poured into water and extracted with diethyl ether. The alcohol product, i.e. oily rac. 5-[2,6,6-trimethyl-3-oxo-4-(phenoxy-acetoxy)-cyclohex-1-en-1-yl]-3-methyl-penta-2,4-dien-1-ol (XV) which remains after evaporation of the ether extract is further reacted as follows:

4.5 g of the alcohol of formula XV obtained above are dissolved in 100 ml of diethyl ether. 2 ml of pyridine are added to the solution at 0° C. and then 1.2 g of phosphorus tribromide are added dropwise. The mixture is stirred for 2 hours and then poured into water and extracted with diethyl ether. The ether extract is evaporated. The residual bromide is taken up in ethyl acetate and 2.9 g of triphenylphosphine are added. The rac. 2(E),4(E)-5-(2,6,6-trimethyl-4-phenoxy-acetyl-3-oxo-cyclohex-1-en-1-yl)-3-methyl-penta-2,4-diene-1-triphenylphosphonium bromide (IIB) which crystallizes out over a period of 24 hrs. melts at 158°–161° C.

EXAMPLE 9

0.005 mol of 2,7-dimethyl-octa-2,6-dien-4-yne-1,8-bis-triphenylphosphonium bromide (IIIB) is added to 0.01 mol of butyl lithium in 300 ml of a 3:1 mixture of diethyl ether: hexane at −30° C., whilst stirring vigorously. After 10 minutes, 0.008 mol of 5-[2,6,6-trimethyl-3-oxo-4(S)-(phenoxy-acetoxy)-cyclohex-1-en-1-yl]-3-methyl-penta-2,4-dien-1-al (IIA) in 100 ml of diethyl ether is added dropwise. The mixture is stirred for 8 hours and then evaporated. The residual 3(S),3'(S)-15,15'-didehydro-astaxanthin diphenoxyacetate, which has a U.V. maximum at 453 nm in chloroform after purification by adsorption on silica gel, is taken up in methanol and the mixture is heated to the boiling point under reflux. The 3(S),3'(S)-15,15'-didehydro-astaxanthin which precipitates on cooling melts at 204°–206° C.

EXAMPLE 10

3.2 g of 3(S),3'(S)-15,15'-didehydro-astaxanthin are dissolved in 500 ml of toluene. 1 g of a partially inactivated palladium catalyst (Lindlar catalyst) and 0.1 ml of quinoline are added and the mixture is shaken in an atmosphere of hydrogen at room temperature and under normal pressure until the calculated amount of hydrogen is absorbed. The catalyst is filtered off. The 3(S),3'(S)-astaxanthin which remains after evaporation of the filtrate at 50° C./12 mm Hg melts, after recrystallizing from methylene chloride/hexane, at 216°–218° C. U.V. maximum: 489 nm (in chloroform).

EXAMPLE 11

9.36 g of 4(R),6(R)-4-hydroxy-2,6,6-trimethyl-cyclohexanone are dissolved in 56 ml of pyridine. 37 ml of acetic anhydride are added and the solution is poured into ice-water after a period of 18 hours at room temperature and then extracted with diethyl ether. The 4(R),6(R)-4-acetoxy-2,6,6-trimethylcyclohexanone (IV) is isolated from the ether extract as a colorless oil.

EXAMPLE 12

11.8 g of the acetoxycyclohexanone of formula IV obtained in Example 11 are dissolved in 22 ml of glacial acetic acid. 10 g of bromine in 22 ml of glacial acetic acid are added dropwise to the solution at 5° C., whilst cooling. The mixture is stirred for 10 minutes, 110 ml of water are slowly added, whilst cooling, and the mixture is then poured into 1000 ml of water and extracted with diethyl ether. The 4(S)-2-bromo-2,6,6-trimethyl-4-acetoxy-cyclohexanone (V) isolated from the ether extract melts, after recrystallization from pentane, at 39°–41° C.

EXAMPLE 13

A mixture consisting of 12.7 g of the bromide of formula V, 115 ml of dry dimethylformamide, 6.4 g of lithium bromide and 9.2 g of lithium carbonate is heated to 80° C. for 1 hour. This mixture is then cooled, poured into ice-water and extracted with dimethyl ether. The 4(S)-2,6,6-trimethyl-4-acetoxy-cyclohex-2-en-1-one (VI) is isolated from the ether extract as a colorless oil, $[\alpha]_D$: −47.5° (c=1 in dimethyl sulfoxide).

EXAMPLE 14

20 ml of methanol, 10 ml of water and 2.0 g of potassium carbonate are added to 2.0 g of the acetoxycyclohexanone of formula VI obtained in Example 13 and the mixture is stirred for 30 minutes at room temperature. The mixture is then poured into water and extracted with diethyl ether. The 4(S)-2,6,6-trimethyl-4-hydroxy-cyclohex-1-en-1-one (VII) is isolated from the ether extract as a colorless oil, $[\alpha]_D$: −49.0° (c=1 in ethanol).

EXAMPLE 15

10 g of the hydroxycyclohexanone of formula VII obtained in Example 14 are dissolved in 65 ml of diethyl ether. 8.7 ml of trimethylamine are added to the solution and then 8.25 ml of trimethylchlorosilane are added dropwise at 0° C. The solution is then poured into water and extracted with diethyl ether. The colorless, oily 4(S)-2,6,6-trimethyl-4-[(trimethyl-silyl)oxy]-cyclohex-2-en-1-one (VIII) isolated from the ether extract boils at 67°–70° C. $[\alpha]_D$: −59° (c=1 in ethanol).

EXAMPLE 16

37.8 g of trimethyl-[(trans-3-methyl-penta-2-en-4-yn-4-yl)oxy]-silane are added dropwise to a Grignard solution prepared from 5.45 g of magnesium chips and 25.6 g of ethyl bromide. The mixture is stirred for 1 hour, 12.6 g of the silyloxy compound of formula VIII obtained in Example 15 in 70 ml of tetrahydrofuran are added and the solution is stirred for a further 16 hours, poured into a saturated aqueous ammonium chloride solution and extracted with diethyl ether. The 4(S)-[2,6,6-trimethyl-1-hydroxy-4-[(trimethylsilyll)oxy]-cyclohex-2-en-1-yl]-3-methyl-1-[(trimethylsilyl)oxy]-penta-2-en-4-yne (IX) isolated from the ether extract is a 1:4 mixture of the two isomers which can be saponified to the corresponding triol in the next reaction step without further purification.

EXAMPLE 17

72 g of trans-3-methyl-penta-2-en-4-yne are dissolved in 250 ml of diethyl ether. 180 ml of trimethylamine are added to the solution at 0° C. and then 81 g of dimethylchlorosilane are added dropwise, after 3 hours the solution is poured into a 5% strength aqueous sodium hydrogen carbonate solution and then extracted with diethyl ether. The trimethyl-[(trans-3-methyl-penta-2-en-4-yn-4-yl)oxy]-silane isolated from the ether extract boils at 70°–75° C./15 mm Hg.

The corresponding cis-compound, from which cis-compounds of formula I can be obtained via the cis-silyl ether of formula IX and subsequent intermediate steps, can be manufactured in a manner analogous to that described hereinbefore by reaction of cis-3-methyl-penta-2-en-4-yne with trimethylchlorosilane. The trimethyl-[(cis-3-methyl-penta-2-en-4-yn-4-yl)oxy]-silane obtained boils at 59°–60° C./16 mm Hg.

EXAMPLE 18

59 g of the trans-disilyl ether of formula IX obtained in Example 16 are dissolved in 1000 ml of methanol. 230 ml of 5% strength aqueous potassium hydroxide solution are added and the solution is stirred for 5 minutes and then poured into a saturated aqueous sodium chloride solution and extracted with diethyl ether. The 5-[2,6,6-trimethyl-1,4-dihydroxy-cyclohex-1-en-1-yl]-trans-3-methyl-penta-2-en-4-yn-1-ol (X) which remains after evaporation of the ether extract is a 4:1 mixture of two isomers which can be characterized as follows:

The 1(R),4(S)-dihydroxy compound present as the main proportion is an oil; $[\alpha]_D = +178.0°$ (c=1 in ethanol); the corresponding 1(S),4(S)-dihydroxy compound is crystalline; melting point: 116°–117° C.; $[\alpha]_D = -144.5°$ (c=1 in ethanol).

EXAMPLE 19

47.8 g of the mixture of the two isomeric triols of formula X obtained in Example 18 are dissolved in 720 ml of methylene chloride. 200 ml of formic acid are added and the solution is stirred for 45 minutes at room temperature and then poured into water and extracted with diethyl ether. The ether extract is evaporated. The residue is taken up in 500 ml of methanol, 100 g of potassium carbonate in 250 ml of water are added and the mixture is stirred for 1 hour and then poured into water and extracted with ethyl acetate. The 5-[2,6,6-trimethyl-3,4-dihydroxy-cyclohex-1-en-1-yl]-3-methyl-penta-2-en-4-yn-1-ol (XI) isolated from the extract is in the form of two isomers which can be resolved by adsorption on silica gel and characterized as follows:

The 3(S),4(R)-dihydroxy compound present as the main proportion is crystalline; melting point: 115°–117° C.; $[\alpha]_D = -101.7°$ (c=1 in ethanol); the corresponding 3(S),4(S)-dihydroxy compound is an oil.

EXAMPLE 20

29.7 g of the isomerization product of formula XI obtained in Example 19 are dissolved in 3000 ml of methylene chloride. 1000 g of manganese dioxide are added and the solution is stirred for 45 minutes and then filtered. The 5-[2,6,6-trimethyl-3-oxo-4(S)-hydroxy-cyclohex-1-en-1-yl]-3-methyl-penta-2-en-4-yn-1-al (XII) which remains after evaporation of the filtrate melts, after recrystallization from ethyl acetate/hexane, at 91°–93° C.

EXAMPLE 21

13.5 g of the ketoaldehyde of formula XII obtained in Example 20 are dissolved in 100 ml of pyridine. 10 g of phenoxyacetic acid chloride are added dropwise to the solution at 0° C. The mixture is stirred for 1 hour at 0° C. and then poured into water and extracted with diethyl ether. The ether extract is washed with 5% strength aqueous sulfuric acid and then with water. The 5-[2,6,6-trimethyl-3-oxo-4(S)-(phenoxyacetoxy)-cyclohex-1-en-1-yl]-3-methyl-penta-2-en-4-yn-1-al (XIV) isolated from the extract is further reacted as follows:

3.8 g of the triply unsaturated aldehyde of formula XIV obtained hereinbefore are dissolved in 70 ml of toluene and hydrogenated under normal pressure and at room temperature using 1.9 g of a partially poisoned palladium catalyst. The hydrogenation is discontinued when 1.1 mol equivalents of hydrogen have been absorbed. The solution is separated off from the catalyst and evaporated. The 5-[2,6,6-trimethyl-3-oxo-4(S)-(phenoxyacetoxy)-cyclohex-1-en-1-yl]-3-methyl-penta-2,4-dien-1-al which remains is the starting compound of formula IIA used in Example 9.

EXAMPLE 22

0.005 mol of 2,7-dimethyl-octa-2,6-dien-4-yne-1,8-ditriphenylphosphonium bromide (IIIB) are added to 0.01 mol of butyl lithium in 300 ml of a 3:1 parts by volume diethyl ether/hexane mixture at −30° C., while stirring vigorously. After 10 minutes, 0.008 ml of 5-[2,6,6-trimethyl-3-oxo-4-acetoxy-cyclohex-1-en-1-yl]-3-methyl-penta-2,4-dien-1-al in 100 ml of diethyl ether are added dropwise to the mixture, the mixture is stirred for 8 hours at room temperature and then evaporated. The 15,15′-didehydro-astaxanthin diacetate which remains shows a U.V. maximum at 453 nm in chloroform.

EXAMPLE 23

12 g of 5-[2,6,6-trimethyl-3-oxo-4-hydroxy-cyclohex-1-en-1-yl]-3-methyl-penta-2,4-dien-1-al are dissolved in 300 ml of diethyl ether. 25 ml of pyridine are added to the solution at 0° C. and 5.0 g of acetyl chloride are then added dropwise. The mixture is poured into ice-water and extracted with diethyl ether. The oily 5-[2,6,6-trimethyl-3-oxo-4-acetoxy-cyclohex-1-en-1-yl]-3-methyl-penta-2,4-dien-1-al (IIA) which remains after evaporation of the ether extract is condensed with the phosphonium salt of formula IIIB as described in Example 22 without further purification.

EXAMPLE 24

13 g of 5-[2,6,6-trimethyl-3-oxo-4(S)-(phenoxyacetoxy)-cyclohex-1-en-1-yl]-3-methyl-penta-2,4-diene-1-triphenyl-phosphonium bromide (IIB) and 0.6 g of 2,7-dimethyl-octa-2,4,6-triene-1,8-dial (IIIA) are dissolved in 200 ml of isopropanol. 7.5 ml of 2-N sodium methylate are added and the solution is stirred for 1 hour at room temperature, poured into water and extracted with methylene chloride. The 3(S),3′(S)-15,15′-didehydro-astaxanthin which remains after evaporation of the extract melts, after recrystallization from chloroform/methanol or pyridine/water, at 204°–206° C.

EXAMPLE 25

5.26 g of 5-[2,6,6-trimethyl-3-oxo-4(S)-(phenoxyacetoxy)-cyclohex-1-en-1-yl]-3-methyl-penta-2,4-diene-1-triphenyl-phosphonium bromide (IIB) and 440 mg of 2,7-dimethyl-octa-2,6-dien-4-yne-1,8-dial (IIIA) are dissolved in 50 ml of methylene chloride and 20 ml of butylene oxide. The solution is stirred for 16 hours at room temperature and then evaporated. The residue is taken up in methylene chloride. The extract is washed twice with water. The 3(S),3′(S)-15,15′-didehydro-astaxanthin diphenoxyacetate which remains after evaporation of the organic phase can be purified by adsorption on silica gel, using a 1:50 ether/methylene chloride mixture as the eluting agent. U.V. maximum: 453 nm in chloroform.

EXAMPLE 26

20 grams of 5-[2,6,6-trimethyl-3-oxo-4(S)-hydroxy-cyclohex-1-en-1-yl]-3-methyl-penta-2,4-dien-1-al (XII) are dissolved in 250 ml of toluene and hydrogenated under normal pressure and at room temperature using 5 g of a partially poisoned palladium catalyst. The hydrogenation is discontinued when 1 mol equivalent of hydrogen has been absorbed. The solution is separated off from the catalyst and evaporated. The 5-[2,6,6,-trimethyl-3-oxo-4(S)-hydroxy-cyclohex-1-en-1-yl]-3-methyl-penta-2,4-dien-1-al which remains is an oil (XIII).

EXAMPLE 27

14 g of the hydroxyketoaldehyde of formula XIII obtained in Example 26 are dissolved in 200 ml of diethyl ether. 20 ml of pyridine are added to the solution at 0° C. and 12 g of phenoxyacetic acid chloride are then added dropwise. The mixture is stirred for 2 hours at 0° C. and then poured into water and extracted with diethyl ether. The 5-[2,6,6-trimethyl-3-oxo-4(S)-(phenoxyacetoxy)-cyclohex-1-en-1-yl]-3-methyl-penta-2,4-dien-1-al (IIA) is isolated from the ether extract.

EXAMPLE 28

2.1 g of the starting compound of formula IIA obtained in Example 27 are dissolved in 40 ml of ethanol. 60 mg of sodium borohydride are added at −30° C. and the solution is stirred for 1 hour and then poured into water and extracted with diethyl ether. The oily 5-[2,6,6-trimethyl-3-oxo-4(S)-(phenoxyacetoxy)-cyclohex-1-en-1-yl]-3-methyl-penta-2,4-dien-1-ol (XV) which remains after evaporation of the ether extract is further reacted as follows:

17 g of the ketoalcohol of formula XV obtained as above are dissolved in 300 ml of diethyl ether. 1 ml of pyridine is added to the solution at 0° C. and 7 ml of phosphorus tribromide are then added dropwise. After 30 minutes, the mixture is poured into a saturated aqueous sodium chloride solution and extracted with diethyl ether. The ether extract is evaporated. The residual bromide—the compound melts after recrystallization from methylene chloride/hexane at 30°–91° C.—is taken up in 300 ml of diethyl ether and 15 g triphenylphosphine are added. The 5-[2,6,6-trimethyl-3-oxo-4(S)-(phenoxyacetoxy)-cyclohex-1-en-1-yl]-3-methyl-penta-2,4-diene-1-triphenylphosphonium bromide (IIC) which precipitates over a period of 24 hours melts at 149°–151° C.

EXAMPLE 29

13 grams of 5-[2,6,6-trimethyl-oxo-4(S)-hydroxy-cyclohex-1-en-1-yl]-3-methyl-penta-2,4-dien-1-al (XIII) are dissolved in 200 ml of diethyl ether. 20 ml of pyridine are added to the solution at 0° C. and 12 g of chloroacetic acid chloride are then added dropwise. The mixture is stirred for 1 hour and then poured into water and extracted with diethyl ether. The 5-[2,6,6-trimethyl-3-oxo-4(S)-(chloroacetoxy)-cyclohex-1-en-1-yl]-3-methyl-penta-2,4-dien-1-al is isolated from the ether extract (IIA).

EXAMPLE 30

6.0 g of the aldehyde of formula IIA obtained hereinbefore are dissolved in 150 ml of ethanol. 180 mg of sodium borohydride are added portionwise at −30° C. and the solution is stirred for 15 minutes and then poured into ice-water and extracted with diethyl ether.

The 5-[2,6,6-trimethyl-3-oxo-4(S)-(chloroacetoxy)-cyclohex-1-en-1-yl]-3-methyl-penta-2,4-dien-1-ol (XV) which remains after evaporation of the ether extract is further reacted as follows:

20 g of the ketoalcohol of formula XV obtained above are dissolved in 300 ml of diethyl ether. 11.05 g of phosphorus tribromide are added dropwise to the solution at 0° C. After 30 minutes the mixture is poured into water and extracted with diethyl ether. The ether extract is evaporated. The residual bromide is taken up in 300 ml of ethyl acetate and 16 g of triphenylphosphine are added. The 5-[2,6,6-trimethyl-3-oxo-4(S)-(chloroacetoxy)-cyclohex-1-en-1-yl]-3-methyl-penta-2,4-diene-1-triphenylphosphonium bromide (IIB) which precipitates over a period of 24 hours is a sticky oil which partially crystallizes after digestion with ethyl acetate.

EXAMPLE 31

Manufacture of a dye preparation suitable for dyeing foodstuffs:

1.0 g of 15,15'-didehydro-astaxanthin, 0.1 g of d,l-α-tocopherol, 0.4 g of arachis oil and 1.0 g of ascorbyl palmitate are dissolved in 50 ml of hot chloroform. The solution is homogenized with 4.1 g of gelatin, 1.7 g of sugar, 1.7 g of yellow dextrin and a solution of 0.2 g of sodium carbonate in 50 ml of water. The homogenized composition is poured onto a sheet, the chloroform is evaporated off in vacuo and the composition is then comminuted.

200 mg of this dye preparation are dissolved in 20 ml of warm water. The solution is then added to the raw materials necessary for producing 1 liter of ice cream, e.g. cream, milk, sugar and gelatin. A raspberry-red ice cream is obtained which can be given a raspberry aroma if desired.

I claim:

1. A compound of the general formula

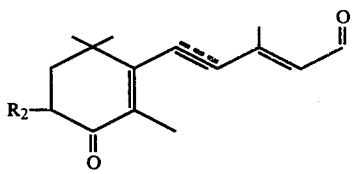

wherein $R_2$ is acyloxy or hydroxy; and the dotted bond can be hydrogenated.

2. The compound of claim 1 wherein said compound is 5-[2,6,6-trimethyl-3-oxo-4-(phenoxyacetoxy)-cyclohex-1-en-1-yl]-3-methyl-penta-2,4-dien-1-al.

3. The compound of claim 1 wherein said compound is 5-[2,6,6-trimethyl-3-oxo-4(S)-(phenoxyacetoxy)-cyclohex-1-en-1-yl]-3-methyl-penta-2,4,-dien-1-al.

4. The compound of claim 1 wherein said compound is 5-[2,6,6-trimethyl-3-oxo-4-(monochloroacetoxy)-cyclohex-1-en-1-yl]-3-methyl-penta-2,4-dien-1-al.

5. The compound of claim 1 wherein said compound is 5-[2,6,6-trimethyl-3-oxo-4(S)-(monochloroacetoxy)-cyclohex-1-en-1-yl)]-3-methyl-penta-2,4-dien-1-al.

6. A compound of the formula

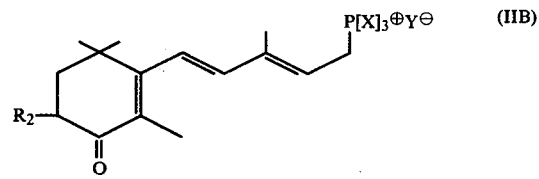

wherein $R_2$ is acyloxy group; X is aryl, and Y is an anion of an inorganic or organic acid.

7. The compound of claim 6 wherein said compound is 5-[2,6,6-trimethyl-3-oxo-4-(phenoxyacetoxy)-cyclohex-1-en-1-yl]-3-methyl-penta-2,4-dien-1-triphenylphosphonium bromide.

8. The compound of claim 6 wherein said compound is 5-[2,6,6-trimethyl-3-oxo-4(S)-(phenoxyacetoxy)-cyclohex-1-en-1-yl]-3-methyl-penta-2,4-dien-1-triphenylphosphonium bromide.

9. The compound of claim 6 wherein said compound is 5-[2,6,6-trimethyl-3-oxo-4-(monochloroacetoxy)-cyclohex-1-en-1-yl]-3-methyl-penta-2,4-diene-1-triphenylphosphonium bromice.

10. The compound of claim 6 wherein said compound is 5-[2,6,6-trimethyl-3-oxo-4(S)-(monochloroacetoxy)-cyclohex-1-en-1-yl]-3-methyl-penta-2,4-diene-1-triphenyl-phosphonium bromide.

11. A compound of the formula

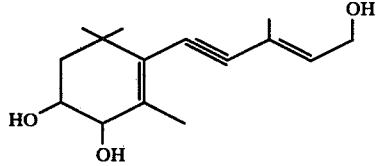

12. A compound of the formula

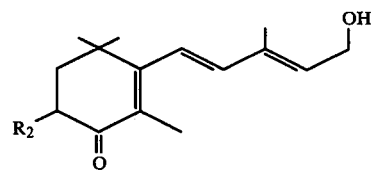

wherein $R_2$ is acyloxy.

13. The compound of claim 12 wherein said compound is 5-[2,6,6-trimethyl-3-oxo-4-(phenoxyacetoxy)-cyclohex-1-en-1-yl]-3-methyl-penta-2,4-dien-1-ol.

* * * * *

UNITED STATES PATENT AND TRADEMARK OFFICE
CERTIFICATE OF CORRECTION

PATENT NO. : 4,156,090
DATED : May 22, 1979
INVENTOR(S) : Frank Kienzle

It is certified that error appears in the above-identified patent and that said Letters Patent are hereby corrected as shown below:

Column 22, claim 9, line 30, "bromice"

> should be

> bromide

Signed and Sealed this

Eleventh Day of August 1981

[SEAL]

*Attest:*

*Attesting Officer*

GERALD J. MOSSINGHOFF

*Commissioner of Patents and Trademarks*